(12) United States Patent
Schultz et al.

(10) Patent No.: US 11,553,160 B1
(45) Date of Patent: Jan. 10, 2023

(54) SYSTEMS AND METHODS FOR IMAGING COMMUNICATION AND CONTROL

(71) Applicant: Avail Medsystems, Inc., Palo Alto, CA (US)

(72) Inventors: David Paul Schultz, Palo Alto, CA (US); Adam Daniel John, Palo Alto, CA (US)

(73) Assignee: AVAIL MEDSYSTEMS, INC., Santa Clara, CA (US)

( * ) Notice: Subject to any disclaimer, the term of this patent is extended or adjusted under 35 U.S.C. 154(b) by 0 days.

(21) Appl. No.: 16/789,255

(22) Filed: Feb. 12, 2020

Related U.S. Application Data (63) Continuation of application No. 15/498,273, filed on Apr. 26, 2017, now abandoned.
(Continued)

(51) Int. Cl.
*H04N 7/18* (2006.01)
*H04N 5/232* (2006.01)
(Continued)

(52) U.S. Cl.
CPC ............... *H04N 7/181* (2013.01); *A61B 1/04* (2013.01); *A61B 6/487* (2013.01); *A61B 8/0883* (2013.01);
(Continued)

(58) Field of Classification Search
CPC .... H04N 7/181; H04N 5/247; H04N 5/23299; H04N 5/2253; H04N 5/23203; A61B 1/04; A61B 6/487; A61B 8/0883; A61B 90/50; A61B 90/361; A61B 2090/373; A61B 2090/376; A61B 2090/364; A61B 2090/371; A61B 2090/372; A61B 2090/378; G16H 30/40; G16H 30/20; G16H 15/00; G16H 80/00; H04W 12/001
(Continued)

(56) References Cited

U.S. PATENT DOCUMENTS 4,473,074 A 9/1984 Vassiliadis
4,585,436 A 4/1986 Davis et al.
(Continued)

FOREIGN PATENT DOCUMENTS

TW 200421149 A 10/2004

OTHER PUBLICATIONS

U.S. Appl. No. 29/562,031 Notice of Allowance dated Nov. 8. 2019.
(Continued)

*Primary Examiner* — Joseph G Ustaris
*Assistant Examiner* — Jimmy S Lee
(74) *Attorney, Agent, or Firm* — Wilson Sonsini Goodrich & Rosati (57) ABSTRACT

A telesurgical mentoring platform with a wheeled base, a lower rack mounted on the base, an upper rack extending vertically from the lower rack, a compactly foldable articulated arm that is configured to extend horizontally outward away from the upper rack and configured to connect to a connector piece holding an end effectuator at its distal end, a tablet personal computer; the console configured to be readily mobilized on the floor of an existing operating room and is capable of providing a connectivity point for communication, audiovisual, and data transfer services in an operating room.

20 Claims, 5 Drawing Sheets

Related U.S. Application Data (60) Provisional application No. 62/328,366, filed on Apr. 27, 2016.

(51) Int. Cl.

| | |
|---|---|
| *H04N 5/247* | (2006.01) |
| *G16H 30/20* | (2018.01) |
| *G16H 30/40* | (2018.01) |
| *G16H 15/00* | (2018.01) |
| *G16H 80/00* | (2018.01) |
| *A61B 1/04* | (2006.01) |
| *A61B 6/00* | (2006.01) |
| *A61B 8/08* | (2006.01) |
| *A61B 90/00* | (2016.01) |
| *A61B 90/50* | (2016.01) |
| *H04N 5/225* | (2006.01) |
| *H04W 12/03* | (2021.01) |

(52) U.S. Cl.
CPC ............ *A61B 90/361* (2016.02); *A61B 90/50* (2016.02); *G16H 15/00* (2018.01); *G16H 30/20* (2018.01); *G16H 30/40* (2018.01); *G16H 80/00* (2018.01); *H04N 5/2253* (2013.01); *H04N 5/23203* (2013.01); *H04N 5/23299* (2018.08); *H04N 5/247* (2013.01); *A61B 2090/364* (2016.02); *A61B 2090/371* (2016.02); *A61B 2090/372* (2016.02); *A61B 2090/373* (2016.02); *A61B 2090/376* (2016.02); *A61B 2090/378* (2016.02); *H04W 12/03* (2021.01)

(58) Field of Classification Search
USPC ........................................................ 348/159
See application file for complete search history.

(56) References Cited

U.S. PATENT DOCUMENTS

| | | | |
|---|---|---|---|
| D285,001 S | 8/1986 | Denis et al. | |
| 4,625,731 A | 12/1986 | Quedens et al. | |
| 4,695,271 A | 9/1987 | Goethel | |
| 4,753,473 A | 6/1988 | Arnett et al. | |
| 4,778,329 A | 10/1988 | Phillips et al. | |
| D387,168 S | 12/1997 | Edelman et al. | |
| 5,701,904 A | 12/1997 | Simmons et al. | |
| 5,872,892 A | 2/1999 | Brown et al. | |
| 5,872,922 A | 2/1999 | Hogan et al. | |
| 5,971,572 A | 10/1999 | Rouchon et al. | |
| D447,567 S | 9/2001 | Murphy et al. | |
| 6,292,713 B1 | 9/2001 | Jouppi et al. | |
| 6,343,601 B1 | 2/2002 | Kiske et al. | |
| D467,001 S | 12/2002 | Buczek et al. | |
| 6,641,039 B2 | 11/2003 | Southard | |
| D486,915 S | 2/2004 | Warschewske et al. | |
| D518,267 S | 3/2006 | Arceta | |
| 7,133,062 B2 | 11/2006 | Castles et al. | |
| 7,164,969 B2 | 1/2007 | Wang et al. | |
| 7,199,817 B2 | 4/2007 | Mottur et al. | |
| D550,362 S | 9/2007 | Olivera et al. | |
| 7,289,883 B2 | 10/2007 | Wang et al. | |
| D567,381 S | 4/2008 | Olivera et al. | |
| 7,411,509 B2 | 8/2008 | Rosenfeld et al. | |
| 7,432,949 B2 | 10/2008 | Remy et al. | |
| 7,562,883 B2 | 7/2009 | Livengood et al. | |
| D613,866 S | 4/2010 | Tanaka et al. | |
| D613,867 S | 4/2010 | Tanaka et al. | |
| 7,761,185 B2 | 7/2010 | Wang et al. | |
| 7,949,616 B2 | 5/2011 | Levy et al. | |
| 8,069,420 B2 | 11/2011 | Plummer | |
| D652,521 S | 1/2012 | Ross et al. | |
| D652,936 S | 1/2012 | Ross et al. | |
| 8,092,426 B2 | 1/2012 | Molnar | |
| 8,179,418 B2 | 5/2012 | Wright et al. | |
| D692,563 S | 10/2013 | Naef et al. | |
| 8,670,017 B2 | 3/2014 | Stuart et al. | |
| 8,780,165 B2 | 7/2014 | Wang et al. | |
| D712,833 S | 9/2014 | George et al. | |
| 8,849,679 B2 | 9/2014 | Wang et al. | |
| 8,849,680 B2 | 9/2014 | Wright et al. | |
| 8,872,879 B2 | 10/2014 | Saleh et al. | |
| 8,897,920 B2 | 11/2014 | Wang et al. | |
| D726,324 S | 4/2015 | Duncan et al. | |
| D734,475 S | 7/2015 | Ross | |
| D735,342 S | 7/2015 | Asad et al. | |
| 9,089,972 B2 | 7/2015 | Stuart et al. | |
| 9,129,054 B2 | 9/2015 | Nawana et al. | |
| 9,160,783 B2 | 10/2015 | Pinter | |
| D743,036 S | 11/2015 | Boukhny et al. | |
| D746,475 S | 12/2015 | Mongin et al. | |
| 9,198,728 B2 | 12/2015 | Wang et al. | |
| D750,787 S | 3/2016 | Asad et al. | |
| D751,209 S | 3/2016 | Dimino et al. | |
| D767,423 S | 9/2016 | Choudhary | |
| D776,279 S | 1/2017 | Newman et al. | |
| 9,600,631 B2 | 3/2017 | Stuart et al. | |
| 9,602,765 B2 | 3/2017 | Wang et al. | |
| D792,974 S | 7/2017 | Roth | |
| D807,510 S | 1/2018 | Newman et al. | |
| D816,232 S | 4/2018 | Asad et al. | |
| 10,315,312 B2 | 6/2019 | Wang et al. | |
| 10,404,939 B2 | 9/2019 | Wang et al. | |
| 10,483,007 B2 | 11/2019 | Celmins et al. | |
| D871,588 S | 12/2019 | Schultz et al. | |
| 10,617,299 B2 | 4/2020 | Sanchez et al. | |
| 10,682,763 B2 | 6/2020 | Pinter | |
| 10,768,668 B2 | 9/2020 | Herzog et al. | |
| 10,887,545 B2 | 1/2021 | Stuart et al. | |
| 2002/0015296 A1 | 2/2002 | Howell et al. | |
| 2005/0052527 A1* | 3/2005 | Remy | H04N 7/181 348/E7.086 |
| 2006/0052676 A1 | 3/2006 | Wang et al. | |
| 2006/0119701 A1 | 6/2006 | King | |
| 2006/0122482 A1 | 6/2006 | Mariotti et al. | |
| 2006/0136703 A1 | 6/2006 | Wisecup et al. | |
| 2007/0122783 A1 | 5/2007 | Habashi | |
| 2007/0192910 A1 | 8/2007 | Vu et al. | |
| 2009/0240371 A1 | 9/2009 | Wang et al. | |
| 2009/0318770 A1 | 12/2009 | Marka et al. | |
| 2010/0115418 A1 | 5/2010 | Wang et al. | |
| 2011/0187875 A1 | 8/2011 | Sanchez et al. | |
| 2011/0190930 A1 | 8/2011 | Hanrahan et al. | |
| 2011/0213210 A1 | 9/2011 | Temby et al. | |
| 2011/0288684 A1 | 11/2011 | Farlow et al. | |
| 2012/0072024 A1 | 3/2012 | Wang et al. | |
| 2012/0098927 A1* | 4/2012 | Sablak | H04N 5/2251 348/E5.042 |
| 2012/0126503 A1 | 5/2012 | Butler et al. | |
| 2012/0191464 A1 | 7/2012 | Stuart et al. | |
| 2012/0303476 A1 | 11/2012 | Krzyzanowski et al. | |
| 2012/0306994 A1 | 12/2012 | Schwartz et al. | |
| 2013/0248458 A1 | 9/2013 | Dehnadi et al. | |
| 2013/0339039 A1 | 12/2013 | Roman et al. | |
| 2014/0095890 A1* | 4/2014 | Mangalore | G06F 21/60 713/189 |
| 2014/0135990 A1* | 5/2014 | Stuart | H04N 5/232933 700/259 |
| 2014/0204190 A1 | 7/2014 | Rosenblatt, III et al. | |
| 2014/0218282 A1 | 8/2014 | Hung et al. | |
| 2014/0263674 A1 | 9/2014 | Cerveny | |
| 2015/0104013 A1* | 4/2015 | Holman | H04L 63/061 380/243 |
| 2015/0339452 A1 | 11/2015 | Wright et al. | |
| 2016/0119593 A1 | 4/2016 | Schultz et al. | |
| 2017/0020627 A1* | 1/2017 | Tesar | A61B 90/361 |
| 2017/0316705 A1* | 11/2017 | Schultz | A61B 34/25 |
| 2019/0147141 A9 | 5/2019 | Kahn | |
| 2019/0328229 A1 | 10/2019 | Sanchez et al. | |
| 2019/0342520 A1 | 11/2019 | Wang et al. | |
| 2020/0101615 A1 | 4/2020 | Pinter et al. | |
| 2020/0203025 A1 | 6/2020 | Kaira et al. | |

(56) References Cited

U.S. PATENT DOCUMENTS

2020/0215683 A1   7/2020   Wright et al.
2020/0237224 A1   7/2020   Sanchez et al.
2020/0265961 A1   8/2020   Celmins et al.

OTHER PUBLICATIONS

U.S. Appl. No. 15/498,273 Office Action dated Jan. 30, 2019.
U.S. Appl. No. 29/562,031 Office Action dated Feb. 4, 2019.
U.S. Appl. No. 29/562,031 Office Action dated Jul. 23, 2018.
U.S. Appl. No. 15/498,273 Office Action dated Aug. 14, 2019.
U.S. Appl. No. 29/562,031 Notice of Allowance dated Aug. 29, 2019.

* cited by examiner

SYSTEMS AND METHODS FOR IMAGING COMMUNICATION AND CONTROL

CROSS-REFERENCE

This application is a continuation application of U.S. application Ser. No. 15/498,273, filed on Apr. 26, 2017, which claims the benefit of U.S. Provisional Application No. 62/328,366, filed on Apr. 27, 2016, all of which are incorporated herein by reference in their entirety.

FIELD

The invention relates to the field of telesurgical mentoring platforms for surgeons and/or medical device representatives.

BACKGROUND

Telesurgical mentoring platforms have evolved as an important subset of telemedicine, yet has remained an under-utilized technique in the operating room.

Telesurgical mentoring typically allows a more experienced surgeon to assist or direct another less experienced surgeon while is operating at a remote location. The benefit is that the more experienced surgeon can assist in a morning surgery in Miami and an afternoon surgery in Los Angeles, while never leaving his practice in New York.

Doctors can also benefit from the advice of device manufacturers representatives during surgery. For example, a doctor that is installing a new type of stent may need some installation guidance from the manufacturer. The manufacturer's representative can provide this guidance without having to travel to the medical room.

One of the primary requirements for conferring telesurgical mentoring is the availability of a clear view of the site of incision on the patient's body for a remote surgeon. When the local surgeon is working, the camera should be easy to adjust and the platform on which it sits must be very mobile to remotely position the camera in various position via controlling the articulated arms.

The art in this field demonstrates a need for the continuous improvement on systems that can provide telesurgical mentoring. For example, U.S. Pat. No. 4,753,473 issued to Arnett describes about a telesurgical gripper for robotic apparatus used for various applications. Also, U.S. Pat. No. 5,872,892 issued to Brown et al. describes a process and apparatus for imparting linear motion to tooling. The tooling is attached to a manipulator device having two different length arms. U.S. Pat. No. 6,343,601 issued to Kiske et al. describes a mobile medical supply device with an anesthesia apparatus, with a plurality of supply and drain lines. U.S. Pat. No. 4,778,329 issued to Phillips describes a robot with an arm and the movement of the arm defined in XY plane.

U.S. Pat. No. 5,971,572 issued to Rouchan a device for the angular positioning of a mass with respect to a horizontal support axis which includes a support arm intended to carry the mass and mounted such that it can be angularly displaced about the support axis.

Most of the articulated arms described in the prior art may be able to do the job of positioning the camera at various positions. But none of the above described articulated arms can move the camera dexterously by infinitely incremental positions. Even if they do so, they would require repeated manual adjustment which would become a labor-intensive task and would be cumbersome.

Accordingly, there exists a need for an articulated arm for a medical mobile cart which can be easily maneuvered to infinitival location displacements and controlled efficiently from a remote location.

SUMMARY

The present invention describes an articulated arm connected to a telesurgical mentoring platform which includes a wheeled base, a lower rack mounted on the base, an upper rack extending vertically upwards from the lower rack, display screens attached to the upper rack and a articulated arm extending from the upper portion of the upper rack.

The telesurgical mentoring platform with an articulated arm as disclosed provides a number of advantages, including perioperative medical device support in the operating room, improved viewing angles and better image quality for doctors and others who are viewing remotely via the electronic display.

In addition, the articulated arm would help in fine controlling of the position of the end effectuator (for example the end effectuator could be a pan tilt zoom camera, special surgery lighting device or the like)

Since the portable platform can be maneuvered around the operating table there is no need for the use of ceiling booms to suspend equipment or the ceiling booms can be reserved for larger equipment that is otherwise too heavy to be supported by a floor standing unit.

Another advantage includes gesture-based control of the pan-tilt-zoom camera for both the users in the operating room and the remote users can manipulate through the use of the tablet device. In addition, the platform provides the ability for users in the operating room and remote user to manipulate the flow of video, audio and data by toggling of video sources, selection of audio output source and selection of data sources.

Further, the stand portion of the unit can be used to store electronic equipment and it provides a centralized-on board computer that can be readily accessed by the surgeon and medical staff. The floor standing console can also be configured to deliver power and electronic connectivity to equipment.

It should be understood that the summary above is provided to introduce in simplified form a selection of examples that are further described in the detailed description. It is not meant to identify key or essential features of any claimed subject matter that may later claim priority to the present description. Furthermore, the scope of any such claimed subject matter would not be limited to implementations that solve any disadvantages noted above or contained herein.

These and other embodiments are described in more detail in the following detailed descriptions and the figures. The foregoing is not intended to be an exhaustive list of embodiments and features of the present invention. Persons skilled in the art are capable of appreciating other embodiments and features from the following detailed description in conjunction with the drawings.

BRIEF DESCRIPTION OF THE DRAWINGS

Many aspects of the present invention can be better understood with reference to the following drawings. The components in the drawings are not necessarily to scale, emphasis instead being placed upon clearly illustrating the principles of the present invention. Moreover, in the drawings like reference numerals designate corresponding parts throughout several views.

SELECTED REFERENCE CHARACTERS

100 Illustrates a perspective view of the telesurgical mentoring platform.
110 Wheeled Base
112, 114, 116, 118 Lockable swivel caster wheels
120 Lower rack
130 Upper rack
145 Electronic display
150 Articulated arm base
155 Electronic display with control capabilities
160 Articulated arm
170 Articulated head
175 Stationary Camera
180 Connecting piece
185 Control handle
190 End effectuator
200 Illustrates a top view of the telesurgical mentoring platform.
300 Illustrates a side view of the telesurgical mentoring platform.
400 Illustrates a side view of the telesurgical mentoring platform with a compactly folded articulated arm.
500 Illustrates a system diagram for the telesurgical mentoring platform.
510A and B Imaging Systems
520 Video Mixer
530A and B Cameras
540 Video Frame Grabber
550 Computer
560A and B Blue Tooth headsets
570 Monitor
580 Power Supply
590 Power mains

DETAILED DESCRIPTION

The embodiments in this disclosure, as illustrated in FIGS. 1 through 4 and described in the text below, are adapted for telesurgical mentoring of operating room surgical procedures, including, but not limited to, orthopedic, spinal, interventional cardiology, peripheral vascular, Neuromodulation, orthopedic, urology and cardiac rhythm management procedures. The different components described in the invention may be made with tube metal or any other suitable material that can be used in a sterile environment such as an operating room.

The term electronic display shall mean an electronic visual display, informally a screen, and a display device for presentation of images, text, or video transmitted electronically, without producing a permanent record. Electronic visual displays may include television sets, computer monitors, tablet computers, smartphones, and information appliances.

The term on-board computer shall mean and represent practically any type of computer, computer system or other programmable electronic device having mobile computing capabilities, including a personal computer, a tablet computer, Personal Digital Assistant (PDA), Personal Information Manager (PIM), cellular telephone, smartphone, and the like.

Figure 1:
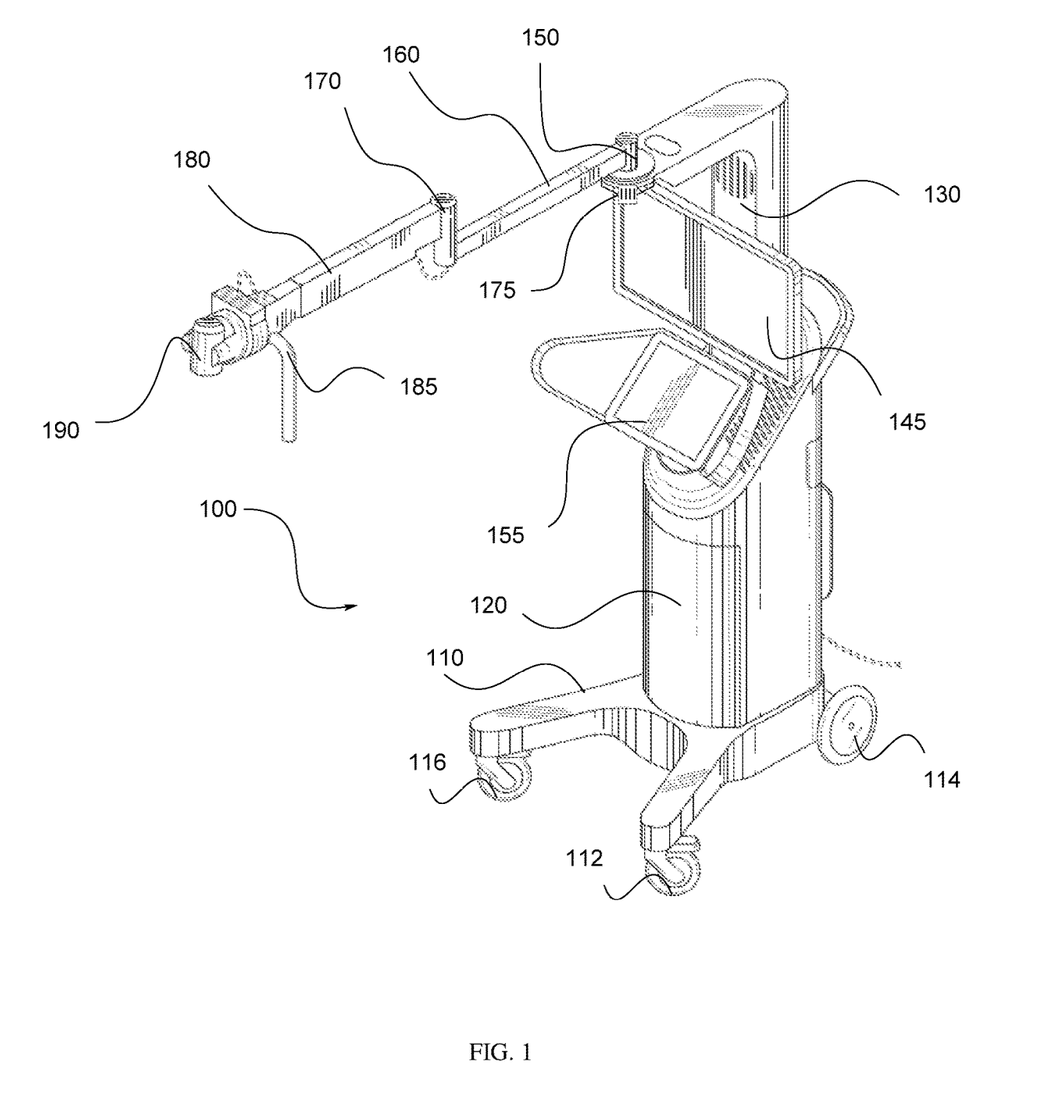
FIG. 1 is a front side, isometric view of a telesurgical mentoring platform with an articulated arm, according to embodiments of the present invention.

In a preferred embodiment, referring to FIG. 1, reference numeral label 100 designates a telesurgical mentoring platform with an articulated arm. Unit 100 has a wheeled base 110 with lockable swivel caster-wheels 112, 114, 116, and 118, a lower rack 120, an upper rack 130, electronic display 145, electronic display with control capabilities 155, articulated arm base 150, articulated arm 160, articulated head 170, a first camera 175, connector piece 180, a handle 185 on the articulated arm and an end effectuator 190.

Referring to FIG. 2 and FIGS. 3, 200 and 300 represent the top plan view and side view respectively of the telesurgical platform. Referring to FIG. 4, 400 represents a side view of the telesurgical platform with a compactly folded articulated arm.

Figure 5:
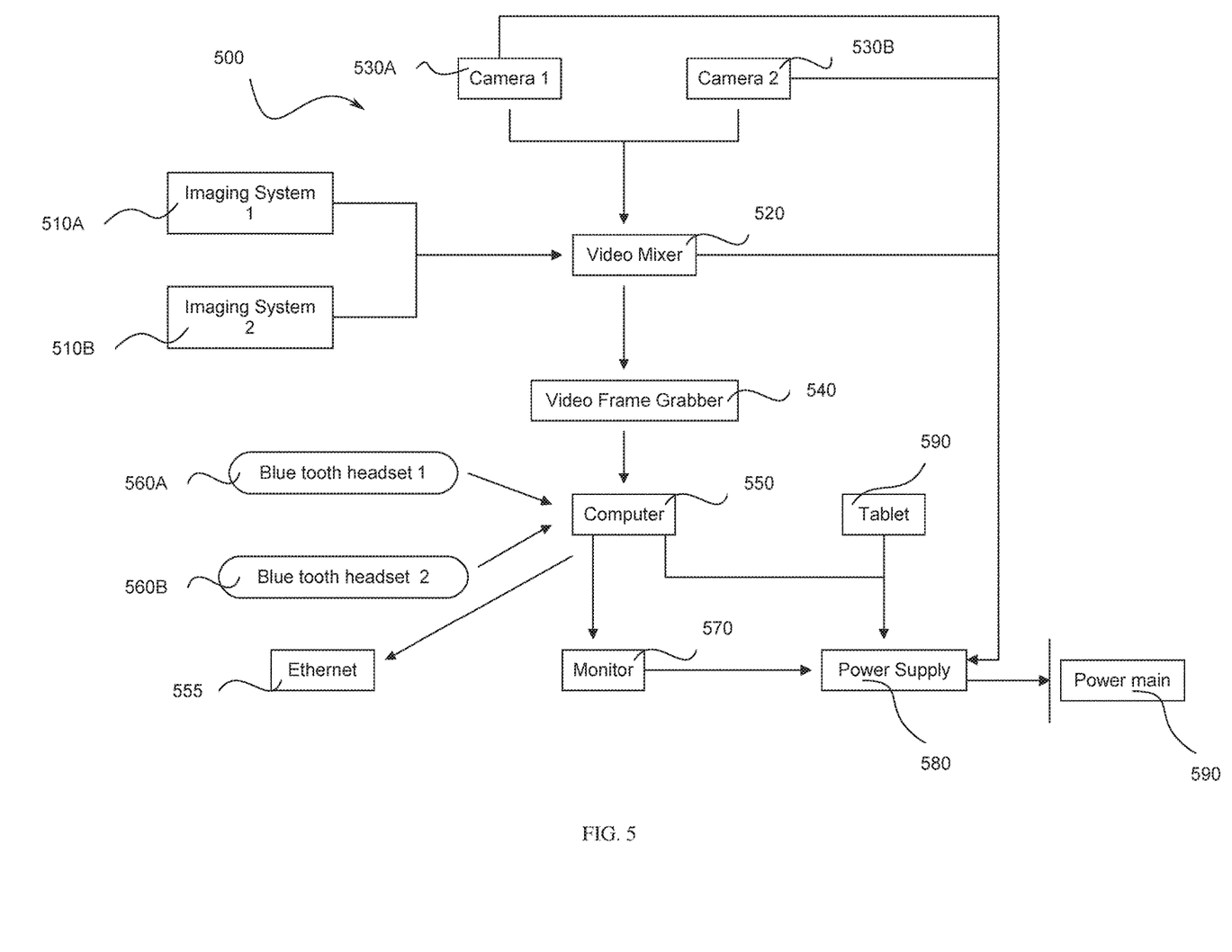
FIG. 5 is a system diagram of the unit shown in FIG. 1.

Referring to FIG. 5, 500 represents a network diagram overview of the components of the telesurgical platform including various components. Imaging systems 510A and 510B are connected to a video mixer 520. The two medical imaging inputs 510A and 510B allows for the ability to directly include the inputs from one or more medical imaging systems in the operating room (e.g., Fluoroscopy, Echocardiogram, Endoscope), encrypt their real-time view and transmit the view out to the remote user. The connection inputs can be DVI, HDMI or SDI. Cameras 530A and 530B also input their recordings into the video mixer 520 which is in turn is connected to a Video Frame Grabber 540. The video mixer 520 allows the unit to toggle various video sources and provide multi-screen functionality (like full screen, split screen, tri-view, quad-view).

A computer 550 takes input from video frame grabber 540 and the videos can be processed on a monitor 570 or a tablet 590. The output of monitor 570 can be in the form of a HDMI monitor output, which allows for the monitor of the unit to be mirrored to existing monitors in the operating room.

The computer 550 is also connected to a blue tooth headsets 560A and 560B. An ethernet connection 555 is linked to the computer, which allows for connecting to the internet. All the above components are powered by a power supply 580 connected to a main power supply 590. The medical power supply 580 and 590 allows the unit to operate without being plugged in for a specified period of time without disruption.

In a non-limiting embodiment, four rolling lockable caster wheels are used with the base 110. Three wheels 112, 114, and 116 are shown in FIG. 1, while the fourth wheel 118 can be visualized in FIG. 2. It should be appreciated by those of ordinary skill that the specific structural and material configurations of the base 110 and caster wheels 112, 114, 116, and 118 are exemplary only. Other design configurations and any number of caster wheels may be used that generally fall within the spirit and scope of the present invention.

With continuing reference to FIG. 1-4, base 110 is connected to lower rack 120 which is in turn connected to the upper rack 130. In a non-limiting embodiment, an articulated arm 160 is attached to the upper rack of the telesurgical platform as shown in shown in FIGS. 1-4. The lower rack 120 can be of hollow construction resembling a lockable cabinet to accommodate a medical power supply, a quad core computer or a video input converter. Optionally the lower rack 120 may also host accessories required for Bluetooth technology headsets (560A and 560B), keyboards, mouse and the like. A handle or hook can be attached to the lower rack 120 for holding on to single use sterile covers for the different electronic accessories.

It should be appreciated by those of ordinary skill that the specific structural and material configurations of articulated arm 160 is exemplary only. Other design configurations and any number of arms may be used that generally fall within the spirit and scope of the present disclosure.

The articulated arm 160 is capable of swinging in a horizontal plane extending from the articulated arm base 150 at the top portion of the upper rack. The articulated arm head 170 is connected to a connector piece 180 of varying length which has an end effectuator 190 connected at the distal end. The articulated arm head 170 is also equipped with the capability of swinging the articulated arm 160 and the connector piece 180 in a horizontal plane extending from the articulated head. The freedom for swinging the articulated arm and the connector piece in a horizontal plane makes way for the compact folding feature of the articulated arm as shown in FIG. 4. The end effectuator can be a pan tilt zoom camera or a special surgery lighting device or the like. By controlling the position of the articulated arm and articulated head the position of the end effectuator can be maneuvered easily to infinitival incremental desired positions for focusing the end effectuator to the area of interest.

In a non-limiting embodiment, the lower rack hosts the control unit, which includes an on-board computer, power supply and control lines junction, with the control lines further connecting the electronic display with control capabilities to the articulated arm and articulated head components. Venting interfaces are provided on specific areas to allow airflow, circulation and prevent overheating. The fixed camera 175 on the unit directly below 150 assists in a 360-degree visualization of the operating room and camera 190 on an articulating arm 180 allows for a direct view of the surgical site and/or procedural back-table of medical instruments.

In another embodiment, the telesurgical platform includes an electronic display 145 and electronic display with control capabilities 155. In one exemplary embodiment, the electronic display 145 and 155 is a tablet computer with a mobile application installed for connection to the Internet over Wi-Fi or 4G, allowing operating room personnel to communicate securely with personnel who are in a remote location.

Figure 3:
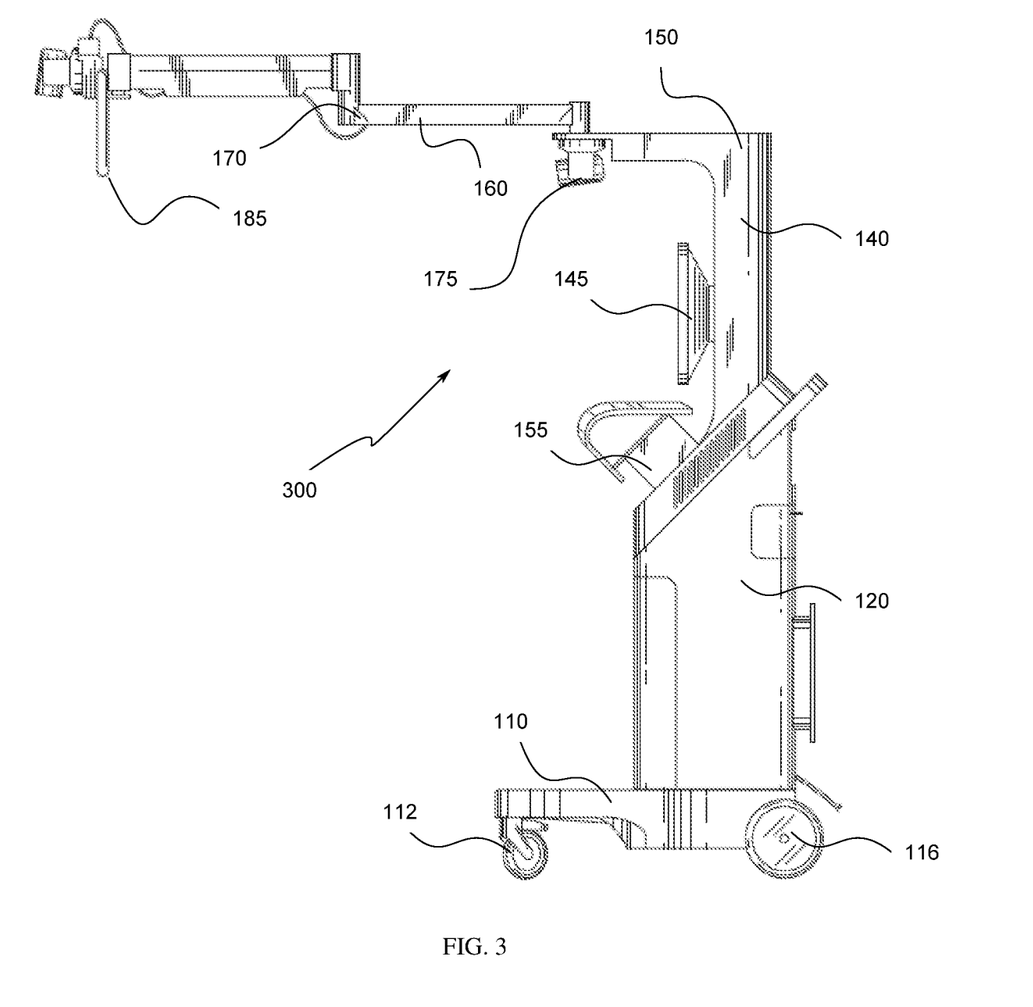
FIG. 3 is a left side view of the unit shown in FIG. 1, the right-side view being a mirror image thereof, according to embodiments of the present invention.
Figure 4:
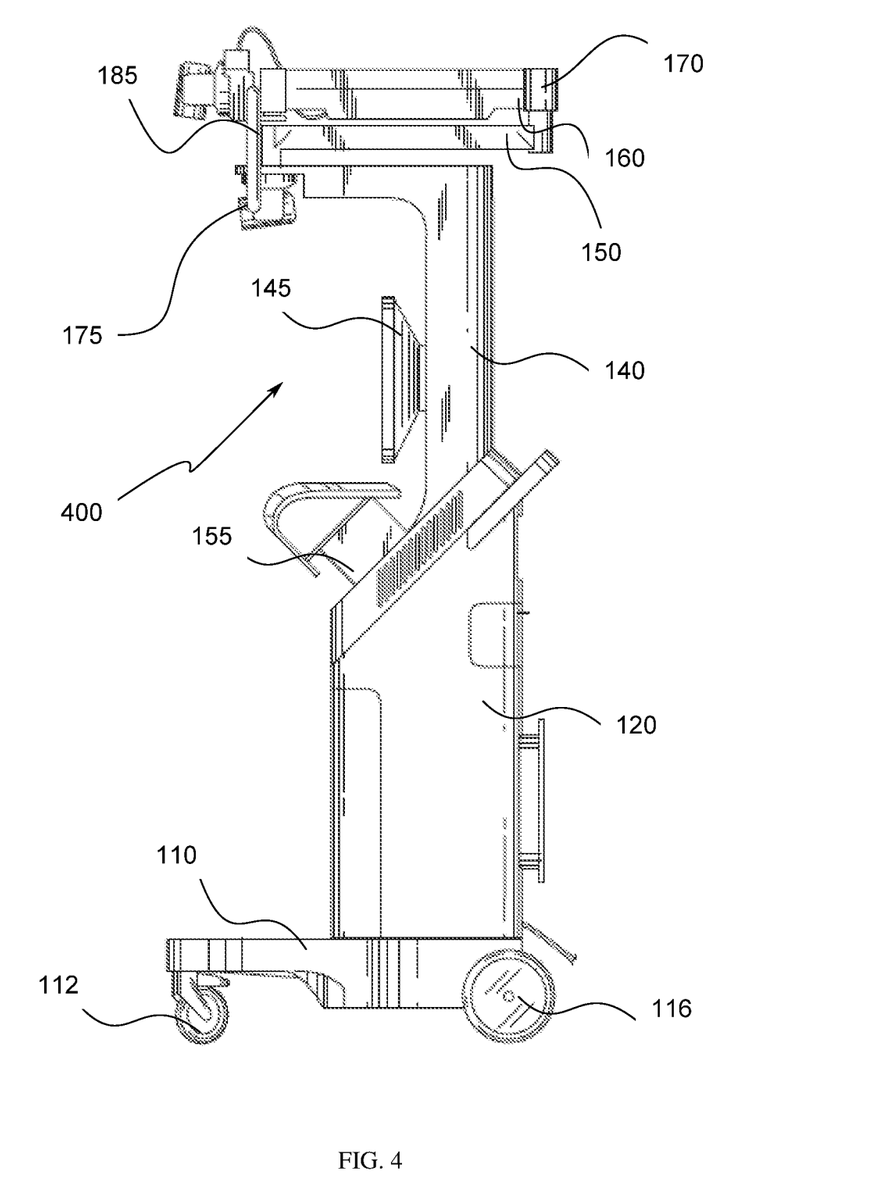
FIG. 4 is a left side view of the unit shown in FIG. 1 and the articulated arm in a folded configuration.

In another preferred embodiment, referring to FIGS. 1 and 3, the electronic display 145 or 155 may have touch-screen control or joy stick or any other form of controlling technique which falls in the scope of the invention.

The on-board computer also typically receives a number of inputs and outputs for communicating information externally. For interface with a user or operator, including doctors and medical staff, the on-board computer typically includes one or more user-input devices (e.g.; a keyboard (not shown), a mouse (not shown), a microphone, or a tablet and an output unit or display (e.g.; an LCD display panel).

Figure 2:
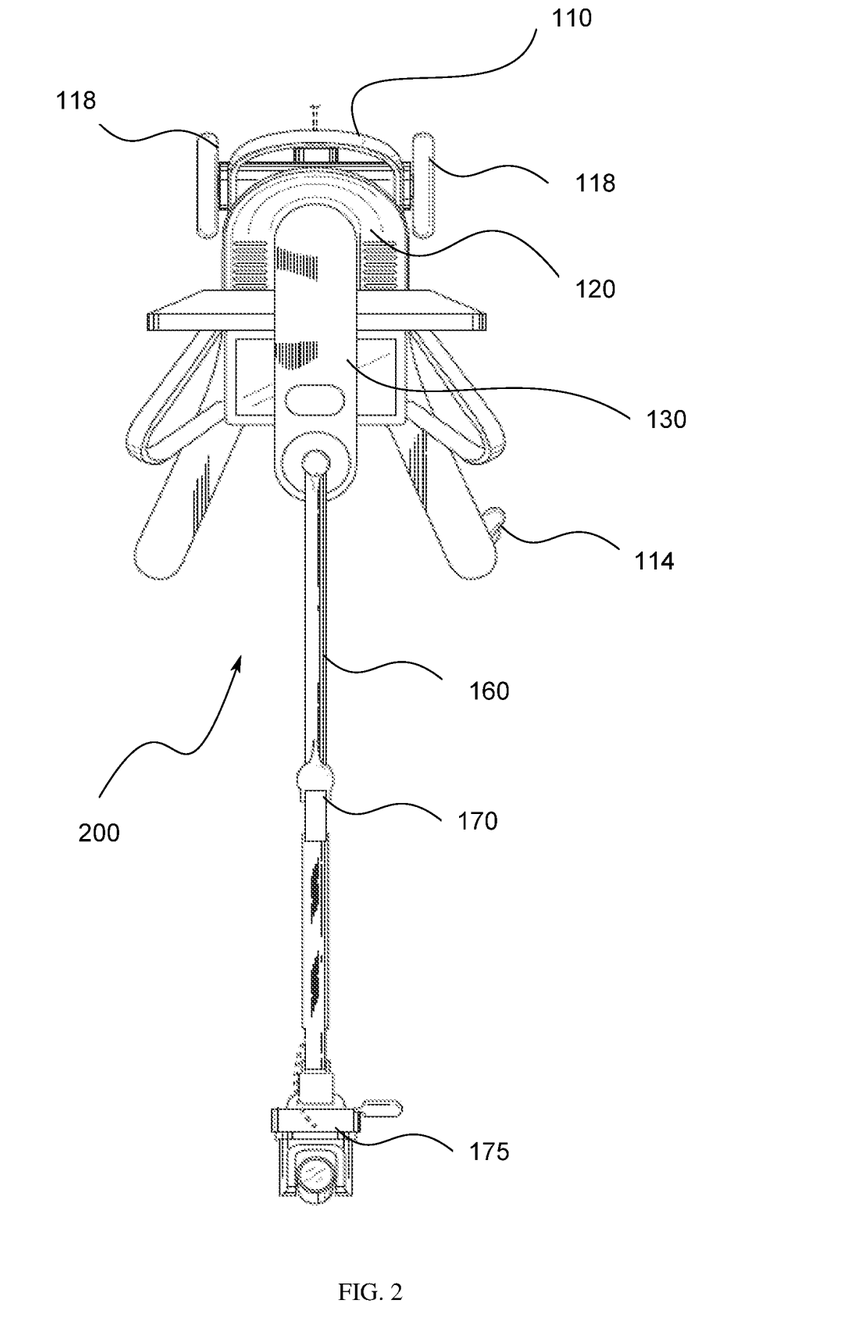
FIG. 2 is a top plan view of the unit shown in FIG. 1, according to embodiments of the present invention.

In a preferred embodiment, with respect to FIGS. 1 through 3, a setup for the telesurgical mentoring platform can be described as follows. The end effectuator camera 190 can be connected to the on-board computer for transmitting a video stream to the on-board computer. In addition, the on-board computer can be capable of converting the video stream to an encrypted stream that may consist of, for example, 128-bit advanced encryption standard. The video stream may be communicated from the on-board computer through the Internet to a remote user via the electronic display 145 or 155.

The many aspects and benefits of the invention are apparent from the detailed description, and thus, it is intended for the following claims to cover all such aspects and benefits of the invention which fall within the scope and spirit of the invention. In addition, because numerous modifications and variations will be obvious and readily occur to those skilled in the art, the claims should not be construed to limit the invention to the exact construction and operation illustrated and described herein. Accordingly, all suitable modifications and equivalents should be understood to fall within the scope of the invention as claimed herein.

What is claimed:

1. An imaging system comprising:
a pan-tilt-zoom camera supported by a distal end of an articulated arm supported by one or more racks on a wheeled base, wherein the articulated arm comprises at least a plurality of pieces configured for free-swinging movement relative to one another, about a vertical axis within a limited horizontal plane, thereby permitting the pan-tilt-zoom-camera to move within the limited horizontal plane relative to the one or more racks;
an additional camera disposed on an upper portion of the one or more racks, wherein the upper portion of the one or more racks comprises a vertical portion and a lateral portion extending horizontally from the vertical portion, wherein the articulated arm and the additional camera are coupled to the lateral portion;
one or more video inputs configured to receive video inputs from additional video sources, said additional video sources comprising at least one of a fluoroscopy imaging system, an echocardiogram imaging system, or an endoscopic imaging system;
one or more processors configured to receive and encrypt images from the pan-tilt-zoom camera, the additional camera, and the one or more video inputs; and
one or more communication systems configured to deliver the images to an electronic display supported by the rack and a remote tablet at a different location from the imaging system, wherein the additional camera is (i) independently movable relative to the electronic display and (ii) positioned in front of the electronic display,
wherein the remote tablet is configured to receive controls from a user to (1) select one or more image sources from the pan-tilt-zoom camera, the additional camera, and the one or more video inputs to display on the tablet; and (2) control movement of the pan-tilt-zoom camera and the articulated arm.

2. The imaging system of claim 1, wherein the electronic display comprises a tablet computer.

3. The imaging system of claim 1, wherein the pan-tilt-zoom camera is angled via the articulating arm to produce live video images on the electronic display.

4. The imaging system of claim 1, wherein the articulating arm is connected to an upper rack of the one or more racks via an articulated arm base, which allows for free-swinging movement of the articulated arm in the limited horizontal plane.

5. The imaging system of claim 1, wherein the articulating arm and a connector piece of the plurality of pieces are connected by an articulated arm base joint allowing for free-swinging movement of the articulated arm and the connector piece in a horizontal plane.

6. The imaging system of claim 1, wherein the imaging system is movable to a convenient location in an operating room or near a patient or a surgical environment.

7. The imaging system of claim 1, wherein the electronic display is configured to display one or more image or video outputs from the pan-tilt-zoom camera.

8. The imaging system of claim 7, wherein the one or more image or video outputs are delivered and transferred via a physical connection or via the Internet.

9. The imaging system of claim 1, further comprising:
an ethernet input for establishing an Internet connection;
an HDMI monitor output for mirroring existing monitors in the imaging system; and
one or more imaging system inputs to directly input the imaging system, encrypt a real-time view obtained using the imaging system, and transmit the real-time view to a remote user.

10. The imaging system of claim 1, further comprising:
a video mixer which allows for toggling of various video sources to provide multi-screen functionality comprising a full screen view, a split screen view, a tri-view, or a quad-view.

11. The imaging system of claim 1, further comprising a power supply, wherein the power supply comprises a rechargeable battery source.

12. The imaging system of claim 1, further comprising a stand-alone speaker and a stand-alone microphone.

13. The imaging system of claim 1, further comprising an on-board computer in communication with the electronic display and an audiovisual component for network conferencing of video content and audio content in real time to a remote user.

14. The imaging system of claim 13, wherein the video content and audio content are delivered and transferred via the Internet to the remote user.

15. The imaging system of claim 1, wherein the upper portion of the one or more racks comprises a lateral extension to which the articulated arm and the additional camera are coupled.

16. The imaging system of claim 1, wherein at least one of the pan-tilt-zoom camera or the additional camera is configured to provide up to a 360-degree visualization of an operating room in which the imaging system is located.

17. The imaging system of claim 1, wherein the articulated arm and the additional camera are coupled to different surfaces or sides of the lateral portion.

18. The imaging system of claim 1, wherein the articulated arm and the additional camera are coupled to opposing surfaces or sides of the lateral portion.

19. The imaging system of claim 1, wherein the images delivered to the electronic display and the remote tablet are manipulable, togglable, or selectable by a remote user and a local user of the imaging system.

20. The imaging system of claim 1, wherein the pan-tilt-zoom camera is configured for gesture-based control by both a remote user and a local user of the imaging system.

* * * * *